United States Patent
Han et al.

(10) Patent No.: US 10,156,512 B2
(45) Date of Patent: Dec. 18, 2018

(54) SYSTEM AND METHOD FOR MEASURING THERMAL RELIABILITY OF MULTI-CHIP MODULES

(71) Applicant: FutureWei Technologies, Inc., Plano, TX (US)

(72) Inventors: Qian Han, San Diego, CA (US); Junsheng Guo, Shenzhen (CN); Yongwang Xiao, Shanghai (CN)

(73) Assignee: FUTUREWEI TECHNOLOGIES, INC., Plano, TX (US)

( * ) Notice: Subject to any disclaimer, the term of this patent is extended or adjusted under 35 U.S.C. 154(b) by 751 days.

(21) Appl. No.: 14/194,029

(22) Filed: Feb. 28, 2014

(65) Prior Publication Data

US 2014/0247857 A1 Sep. 4, 2014

Related U.S. Application Data

(60) Provisional application No. 61/771,437, filed on Mar. 1, 2013.

(51) Int. Cl.
*G01K 7/01* (2006.01)
*G01N 17/00* (2006.01)
*G01R 31/28* (2006.01)

(52) U.S. Cl.
CPC ....... *G01N 17/002* (2013.01); *G01R 31/2874* (2013.01); *G01R 31/2856* (2013.01)

(58) Field of Classification Search
CPC ........ G01K 7/01; G01K 7/015; G01K 15/005; G01K 2217/00; G01K 7/00; G01K 5/486; G01K 7/006; G01K 7/346; G01K 7/425

(Continued)

(56) References Cited

U.S. PATENT DOCUMENTS

| | | | | |
|---|---|---|---|---|
| 4,696,578 A | * | 9/1987 | Mansuria | G01N 25/18 257/E21.53 |
| 5,587,882 A | * | 12/1996 | Patel | H01L 23/3675 257/713 |

(Continued)

FOREIGN PATENT DOCUMENTS

| | | | | |
|---|---|---|---|---|
| DE | 10335314 A1 | * | 2/2004 | H01L 23/34 |
| FR | 2911975 A1 | * | 8/2008 | G06F 17/50 |

OTHER PUBLICATIONS

Jedec Standard. Hybrids/MCM JESD93. Sep. 2005 (reaffirmed: Jan. 2009) Jedec Solid State Technology Association, 24 pages.

(Continued)

*Primary Examiner* — Gail Kaplan Verbitsky
(74) *Attorney, Agent, or Firm* — Slater Matsil, LLP

(57) ABSTRACT

Embodiments are provided herein for testing multichip module (MCM) thermal reliability. An embodiment method includes selecting a chip with higher thermal risk from a plurality of chips in the MCM, and measuring a plurality of predetermined temperature parameters associated with the selected chip. A thermal resistance is then calculated using the predetermined temperature parameters. The thermal resistance is used to determine a thermal performance of the MCM. The predetermined temperature parameters include a junction temperature of the selected chip and at least one of a case temperature above the selected chip, a board temperature below the selected chip, and an ambient air temperature.

20 Claims, 4 Drawing Sheets

(58) Field of Classification Search
USPC .................. 374/178, 183, 185, 44, 29, 30
See application file for complete search history.

(56) References Cited

U.S. PATENT DOCUMENTS

| | | | | |
|---|---|---|---|---|
| 5,713,666 | A * | 2/1998 | Seelin | G01J 5/0003 374/121 |
| 5,927,853 | A * | 7/1999 | Christiaens | G01N 25/18 374/43 |
| 5,931,580 | A * | 8/1999 | Wyland | G01K 7/01 374/141 |
| 6,104,611 | A * | 8/2000 | Glover | F28D 15/06 165/104.33 |
| 6,750,664 | B2 * | 6/2004 | Lance | G01N 25/72 324/670 |
| 6,786,639 | B2 * | 9/2004 | Covi | G01K 7/00 324/525 |
| 6,992,499 | B2 * | 1/2006 | Kunihiro | G01R 31/2894 324/762.05 |
| 7,004,243 | B1 * | 2/2006 | Babcock | G05D 23/1904 165/185 |
| 7,114,556 | B2 * | 10/2006 | Hamilton | G01R 31/2874 165/247 |
| 7,230,334 | B2 * | 6/2007 | Andry | H01L 23/473 165/170 |
| 7,478,303 | B2 * | 1/2009 | Hopkins | H04L 12/40052 714/734 |
| 8,009,420 | B1 * | 8/2011 | Hill | G06F 1/20 257/686 |
| 8,081,473 | B2 * | 12/2011 | Cipolla | H01L 23/4093 165/104.33 |
| 8,087,823 | B2 * | 1/2012 | Aube | G01K 7/01 374/100 |
| 8,375,344 | B1 * | 2/2013 | McGowan | G06F 17/5054 716/100 |
| 8,449,173 | B1 * | 5/2013 | Strong | G06F 11/24 324/500 |
| 8,516,433 | B1 * | 8/2013 | McCracken | G06F 17/5054 326/37 |
| 8,602,645 | B2 * | 12/2013 | Miyamoto | G01K 7/01 323/907 |
| 8,708,560 | B2 * | 4/2014 | Kraemer | H05B 33/0803 250/494.1 |
| 9,490,003 | B2 * | 11/2016 | Shoemaker | G01K 3/08 |
| 9,795,006 | B2 * | 10/2017 | Hirth | G01J 1/44 |
| 2002/0173930 | A1 * | 11/2002 | Perner | G01K 7/01 702/130 |
| 2004/0083075 | A1 * | 4/2004 | Fan | G01K 7/01 702/129 |
| 2006/0038281 | A1 * | 2/2006 | Colgan | H01L 25/0655 257/706 |
| 2007/0210446 | A1 * | 9/2007 | Andry | H01L 23/473 257/714 |
| 2008/0042264 | A1 * | 2/2008 | Colgan | H01L 23/367 257/712 |
| 2008/0140351 | A1 * | 6/2008 | Kerkman | G01K 7/425 702/182 |
| 2008/0234953 | A1 * | 9/2008 | Ignowski | G06F 1/206 702/60 |
| 2008/0238466 | A1 * | 10/2008 | Lopez | G01K 1/16 324/750.28 |
| 2008/0267258 | A1 * | 10/2008 | Hokenmaier | G01K 7/425 374/166 |
| 2008/0310117 | A1 * | 12/2008 | Coico | H01L 21/4871 361/709 |
| 2008/0315403 | A1 * | 12/2008 | Andry | H01L 23/473 257/713 |
| 2009/0154525 | A1 * | 6/2009 | Dai | G01K 7/01 374/178 |
| 2009/0277616 | A1 * | 11/2009 | Cipolla | F28D 15/0233 165/104.33 |
| 2009/0284921 | A1 * | 11/2009 | Colgan | H01L 23/473 361/699 |
| 2010/0150202 | A1 * | 6/2010 | Asano | G01K 7/01 374/44 |
| 2011/0182324 | A1 * | 7/2011 | Stoisiek | G01K 7/16 374/185 |
| 2012/0049341 | A1 * | 3/2012 | Bezama | H01L 23/3675 257/713 |
| 2012/0153454 | A1 * | 6/2012 | Liu | H01L 23/38 257/712 |
| 2012/0201272 | A1 * | 8/2012 | Schuler | G01K 7/16 374/183 |
| 2012/0326294 | A1 * | 12/2012 | Sikka | H01L 23/10 257/704 |
| 2013/0223475 | A1 * | 8/2013 | Yoon | G01R 31/2642 374/57 |
| 2014/0140364 | A1 * | 5/2014 | Charles | G01K 7/01 374/1 |
| 2015/0109750 | A1 * | 4/2015 | Elkaslassy | H05K 1/181 361/782 |
| 2015/0243577 | A1 * | 8/2015 | Yang | H01L 23/36 257/712 |

OTHER PUBLICATIONS

Romig, M., et al., "Methods of Estimating Component Temperatures, Part 1," Texas Instruments, Electronic Engineering Journal, Jul. 14, 2011, 5 pages.

Romig, M., et al., "Methods of Estimating Component Temperatures, Part 2—Case Temperature," Texas Instruments, Electronic Engineering Journal, Jul. 21, 2011, 4 pages.

Romig, M., et al., "Methods of Estimating Component Temperatures, Part 3—Board Temperature," Texas Instruments, Electronic Engineering Journal, Jul. 28, 2011, 4 pages.

* cited by examiner

SYSTEM AND METHOD FOR MEASURING THERMAL RELIABILITY OF MULTI-CHIP MODULES

This application claims the benefit of U.S. Provisional Application No. 61/771,437 filed on Mar. 1, 2013 by Qian Han et al. and entitled "Multichip Module Thermal Reliability Test Method and System," which is hereby incorporated herein by reference as if reproduced in its entirety.

TECHNICAL FIELD

The present invention relates to integrated chip (IC) technology reliability testing, and, in particular embodiments, to a system and method for measuring thermal reliability of multi-chip modules.

BACKGROUND

A multichip module (MCM) generally is a device that contains two or more microcircuits, such as any combination of integrated circuits, discrete semiconductor devices, passive chips, passive on-substrate elements, and the like. In a MCM package, the multiple components are disposed on a unifying substrate so that the MCM physically functions as a single component. Packaging multiple integrated circuits (ICs), semiconductor dies or other discrete components onto a unifying substrate facilitates their use as a single component (as though a larger IC). The MCM package is often referred to as a "chip" in designs, thus illustrating its integrated nature. The MCMs come in a variety of forms depending on design complexity and development. These can range from using pre-packaged ICs on a small printed circuit board (PCB) to fully custom chip packages integrating many chip dies on a High Density Interconnection (HDI) substrate. One of the reliability test processes for MCMs is measuring thermal reliability. Currently, this is achieved by performing many temperature measurements of different parts and configurations and then using the resulting measurement data to assess the thermal reliability in some statistical analysis. This approach is complicated, unreliable, and time/cost consuming. There is a need for an efficient scheme for measuring and assessing thermal reliability of MCMs.

SUMMARY OF THE INVENTION

In accordance with an embodiment, a method by an apparatus for testing thermal reliability of a multichip module (MCM) includes selecting a chip from a plurality of chips in the MCM. A plurality of predetermined temperature parameters associated with the selected chip are then measured. The method further includes calculating a thermal resistance value using the predetermined temperature parameters.

In accordance with another embodiment, a method by an apparatus for testing thermal reliability of a MCM includes selecting a chip with higher thermal risk from a plurality of chips in the MCM, and measuring a plurality of predetermined temperature parameters associated with the selected chip. A thermal resistance is then calculated using the predetermined temperature parameters. The method further includes determining thermal performance of the MCM according to the thermal resistance.

In accordance with yet another embodiment, an apparatus for testing thermal reliability of a multichip module (MCM) includes at least one processor and a non-transitory computer readable storage medium storing programming for execution by the at least one processor. The programming includes instructions to select a chip from a plurality of chips in the MCM and measure a plurality of predetermined temperature parameters associated with the selected chip. The apparatus is further configured to calculate a thermal resistance value using the predetermined temperature parameters.

The foregoing has outlined rather broadly the features of an embodiment of the present invention in order that the detailed description of the invention that follows may be better understood. Additional features and advantages of embodiments of the invention will be described hereinafter, which form the subject of the claims of the invention. It should be appreciated by those skilled in the art that the conception and specific embodiments disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawing, in which.

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF ILLUSTRATIVE EMBODIMENTS

Figure 1:
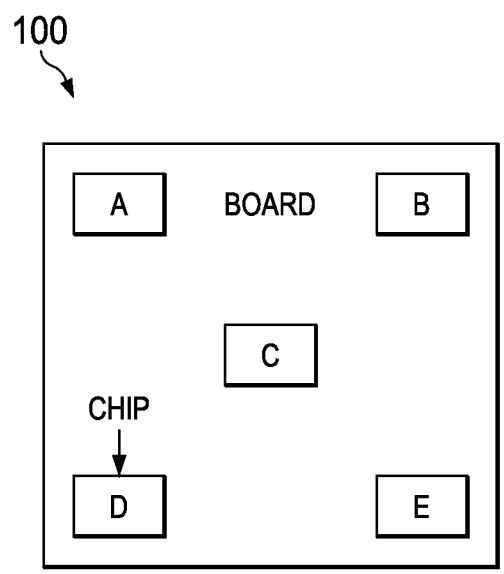
FIG. 1 illustrates a top view of a MCM with multiple chips.

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Currently, there is no specific solution for identifying a MCM's thermal performance, so customers of MCMs do not have any data to evaluate and compare the thermal performance of MCM's. For example, the chips and packaging parameters may be simulated, such as dimensions, material, layout, and thermal specification. Alternatively, all chips in the MCM are tested to assess the thermal performance. Some approaches use the average junction temperature, which may not be a reliable measure. Having thermal reliability data to understand the properties of MCMs would be useful to MCM original equipment manufacturers (OEMs), end users, or other parties. This information also would be useful to OEMs in performing the design and assembly of their own products incorporating such MCMs. Embodiments are provided herein for testing MCM thermal reliability. An embodiment measures thermal parameters of the MCM, such as junction temperature, case temperature, operating ambient temperature, thermal resistance, and the like. Customers of MCMSs may use these properties to evaluate and compare different MCMs.

In an embodiment, the thermal performance of MCM is well defined and can be used by a customer for further evaluation or assembly. The thermal properties of a MCM, are defined, which can be used in design, calculation and evaluation of the thermal reliability. A MCM user can implement a defined method for measuring thermal reliability of a MCM, as described below, in their product assembly. As such, a customer can test a MCM many (e.g., thousands of) times to find out if the product can be used or meets their requirements. The system and method renders the thermal reliability property measurable, comparable and suitable for evaluation for different users. A common test board can be used to implement the schemes herein, as described below, without the need for a special design for each MCM, which reduces cost. Typically, MCMs may be used in terminal products such as in information technology (IT) products, telecommunications products, automotive electronic products, and the like. The embodiments herein may be used by the manufacturers of these products, as well as by the manufacturers of the MCMs themselves.

Junction temperature generally refers to the temperature of the silicon die within a device package when the device is powered. A thermal diode circuit or digital thermal sensor integrated into a chip may be used to provide the junction temperature of a device. Case temperature generally refers to the temperature of the top of the MCM package case. A thermocouple attached to the case of a device, or embedded in a heat sink attached to the case, may be used to provide case temperature. Alternatively, an infrared (IR) camera or gun may be used to provide case temperature of a device. Board temperature is similar to case temperature, except that it is measured on the bottom of the package where it interfaces with a circuit board. Ambient temperature generally refers to the temperature of the surrounding environment (e.g., air) when the device is powered, and can be measured with a digital thermometer or a thermocouple.

Figure 2:
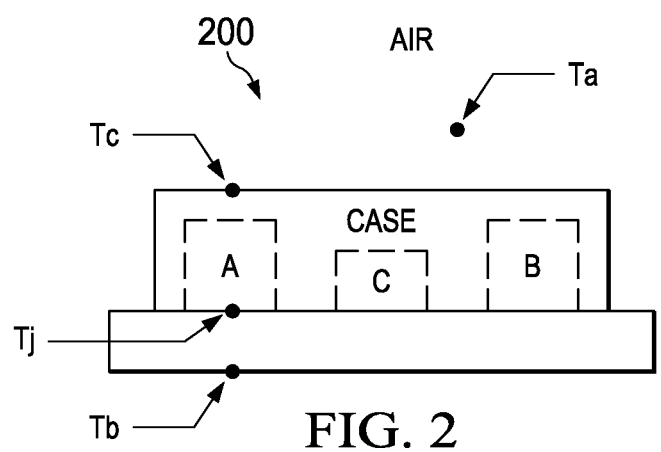
FIG. 2 illustrates a side view of the MCM of FIG. 1.

FIG. 1 shows a top view of a MCM 100 with five chips (A-E) mounted on a substrate or board. Alternatively, the MCM 100 may have two, three, four, or more than five chips. FIG. 2 shows a side view of the MCM 100. As shown, the chips are covered by a case on the board (or substrate). The user of the MCM 100 generally does not have access to measure the junction temperatures of the individual chips within the device. Further, because there are multiple devices spread out across the supporting substrate, the case temperature and the board temperature can vary widely across the extent of the MCM.

To determine junction temperature (Tj) of the MCM 100, the chip with the highest thermal risk (most thermally challenged chip), or one that has an embedded temperature sensor, is selected for measurement. If multiple devices have embedded temperature sensors, the one with the highest thermal risk may be selected. For example, if chip A has an embedded temperature sensor, or it has the highest thermal risk, the chip A is selected as the monitoring chip, and chip A's case temperature is used as the junction temperature of the MCM 100. If not available, a temperature sensor is embedded in or thermally coupled to the selected chip. The chip with the highest power can be, for instance, the chip that has highest power and/or heat density. A chip may have low power, but, with small footage, its power density is high. Such chip can have high thermal risk. Alternatively, a chip that has very strict operation temperature requirement can have high thermal risk. For example, a chip with junction temperature 65° C. can have higher risk than a chip with 85° C. junction temperature requirement. For case temperature (Tc), the MCM cover temperature above the selected chip's (e.g., chip A's) center is used as the case temperature of the MCM 100. For board temperature (Tb), the MCM board temperature below the selected chip's (e.g., chip A's) bottom center is used as the board temperature of the MCM 100. This scheme thus provides a measurable and consistent way to determine a junction temperature, case temperature and board temperature of a MCM.

Figure 3:
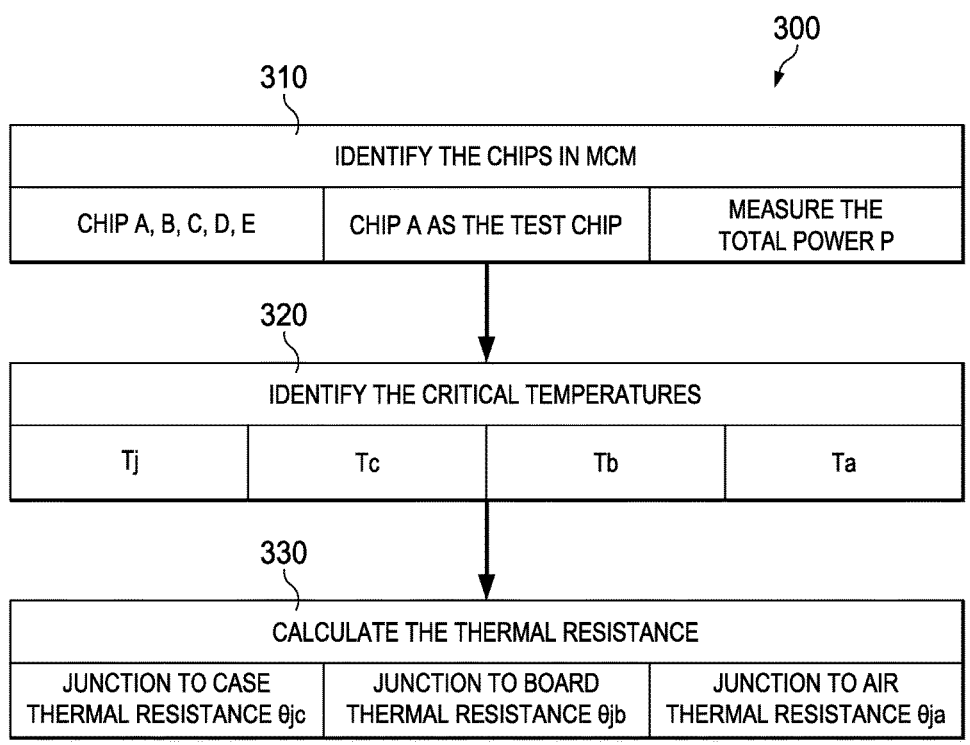
FIG. 3 illustrates a flow chart of an embodiment algorithm for measuring thermal reliability of a MCM.

FIG. 3 illustrates a flow for an embodiment of a defined algorithm 300 for measuring thermal reliability of a MCM, such as the MCM 100. At a first step 310, the chips in the MCM are identified and the chip with the highest thermal risk, or that has an embedded temperature sensor, is selected. After selecting the chip (e.g., chip A of MCM 100), the total power P needed for the MCM 100 is measured. At a next step 320, a plurality of temperature parameters are measured. The measured values include the junction temperature (Tj) which is measured for the selected chip (A), the case temperature (Tc) which is measured for the case, the board temperature (Tb) which is measured for the board, and ambient air temperature (Ta) which can be obtained under steady state test conditions. At the next step 330, relevant thermal resistance values are measured. The thermal resistance values include the junction to case thermal resistance θjc as $$\theta jc = \frac{Tj - Tc}{TotalPower},$$

the junction to board thermal resistance θjb as $$\theta jb = \frac{Tj - Tb}{TotalPower},$$

and the junction to air thermal resistance θja as $$\theta ja = \frac{Tj - Ta}{TotalPower}.$$

The thermal resistance values are used to assess the thermal reliability or performance of the entire MCM (e.g., as one package). For example, each of these values is compared to a benchmark or threshold value, or to corresponding values of other MCMs, for quality evaluation or comparison.

Figure 4:
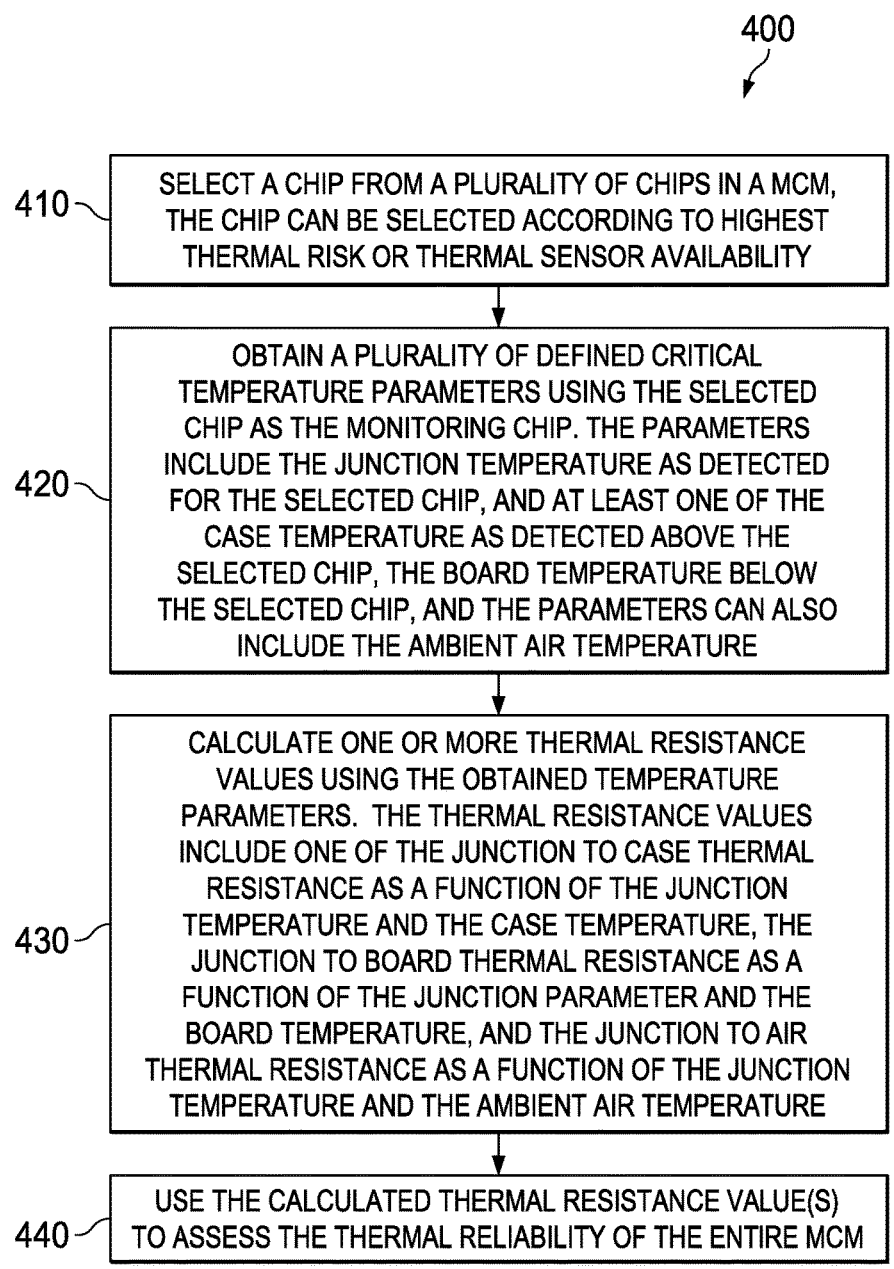
FIG. 4 illustrates an embodiment method for measuring thermal reliability of a MCM.

FIG. 4 shows an embodiment method 400 for measuring thermal reliability of a MCM, such as the MCM 100. The method 400 may comprise the algorithm 300 or a suitable variation of the algorithm. At step 410, a chip is selected from a plurality of chips in a MCM. The chip can be selected according highest thermal risk or thermal sensor availability. For example, the thermal risk can be determined according to power requirement, heat density, operation temperature requirement, or combinations thereof. At step 420, a plurality of defined critical temperature parameters are obtained using the selected chip as the monitoring chip. The parameters can include the junction temperature as detected for the selected chip, the case temperature as detected above the selected chip, and the board temperature below the selected chip. The parameters can also include the ambient air temperature, e.g., above or below the selected chip. At step 430, one or more thermal resistance values are calculated using the obtained temperature parameters. As described above, the thermal resistance values can include the junction to case thermal resistance as a function of the junction temperature and the case temperature, the junction to board thermal resistance as a function of the junction parameter and the board temperature, and/or the junction to air thermal resistance as a function of the junction temperature and the ambient air temperature. At step 440, the calculated thermal resistance value(s) are used to assess the thermal reliability of the entire MCM.

Figure 5:
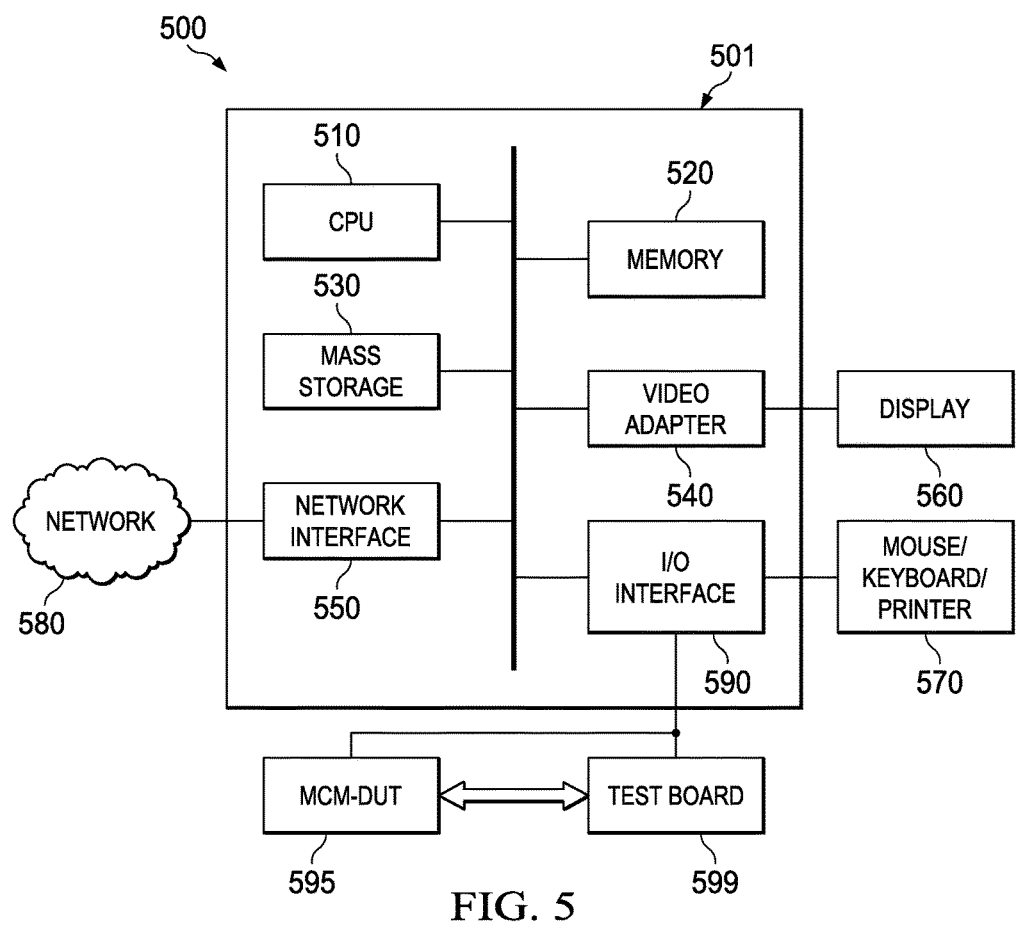
FIG. 5 is a diagram of a processing system that can be used to implement various embodiments.

FIG. 5 is a block diagram of a processing system 500 that may be used for implementing the embodiments and methods disclosed herein, such as a measurement or assessment device for thermal reliability of a MCM. Specific devices may utilize all of the components shown, or only a subset of the components, and levels of integration may vary from device to device. Furthermore, a device may contain multiple instances of a component, such as multiple processing units, processors, memories, transmitters, receivers, etc. The processing system 500 may comprise a processing unit 501 equipped with one or more input/output devices, such as a speaker, microphone, mouse, touchscreen, keypad, keyboard, printer, display, and the like. The processing unit 501 may include a central processing unit (CPU) 510, memory 520, a mass storage device 530, a video adapter 540, and an I/O interface 590 connected to a bus.

The bus may be one or more of any type of several bus architectures including a memory bus or memory controller, a peripheral bus, video bus, or the like. The CPU 510 may comprise any type of electronic data processor. The memory 520 may comprise any type of system memory such as static random access memory (SRAM), dynamic random access memory (DRAM), synchronous DRAM (SDRAM), read-only memory (ROM), a combination thereof, or the like. In an embodiment, the memory 520 may include ROM for use at boot-up, and DRAM for program and data storage for use while executing programs.

The mass storage device 530 may comprise any type of storage device configured to store data, programs, and other information and to make the data, programs, and other information accessible via the bus. The mass storage device 530 may comprise, for example, one or more of a solid state drive, hard disk drive, a magnetic disk drive, an optical disk drive, or the like.

The video adapter 540 and the I/O interface 590 provide interfaces to couple external input and output devices to the processing unit 501. As illustrated, examples of input and output devices include a display 560 coupled to the video adapter 540 and a combination of mouse/keyboard/printer 570 coupled to the I/O interface 590. Other devices may be coupled to the processing unit 501, and additional or fewer interface cards may be utilized. For example, a serial interface such as Universal Serial Bus (USB) (not shown) may be used to provide an interface for a printer.

The processing unit 501 also includes one or more network interfaces 550, which may comprise wired links, such as an Ethernet cable or the like, and/or wireless links to access nodes or one or more networks 580. The network interface 550 allows the processing unit 501 to communicate with remote units via the networks 580. For example, the network interface 550 may provide wireless communication via one or more transmitters/transmit antennas and one or more receivers/receive antennas. In an embodiment, the processing unit 501 is coupled to a local-area network or a wide-area network for data processing and communications with remote devices, such as other processing units, the Internet, remote storage facilities, or the like.

Further, the processing system 500 is coupled to a MCM device under test (DUT) 595 and to a test board 599 on which the MCM is mounted. The computing device is coupled to the MCM and the test board for measuring the junction temperature, case temperature and board temperature of the MCM using e.g., thermal sensors, thermocouples, etc., as described above. The computing device also may measure the ambient temperature.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A method performed by an apparatus for testing a multichip module (MCM), the method comprising:
   selecting a chip from a plurality of chips in the MCM;
   measuring a plurality of predetermined temperature parameters associated with the selected chip, the measuring including detecting a junction temperature for the selected chip and one or more of:
      an ambient air temperature;
      a case temperature of the selected chip; or
      a board temperature of a board on which the selected chip is mounted;
   calculating a thermal resistance value for the MCM using the predetermined temperature parameters, the calculating including calculating one or more of:
      a junction to air thermal resistance as a difference of the junction temperature and the ambient air temperature, weighted by a total power for the MCM;
      a junction to case thermal resistance as a difference of the junction temperature and the case temperature, weighted by the total power for the MCM; or
      a junction to board thermal resistance as a difference of the junction temperature and the board temperature, weighted by the total power for the MCM; and
   comparing the MCM to another MCM using the calculated thermal resistance value for the MCM.

2. The method of claim 1, wherein selecting the chip includes:
   determining power densities for the plurality of chips in the MCM; and
   determining a chip with a highest power density from the plurality of chips.

3. The method of claim 1, wherein selecting the chip is based on at least one of power requirements, heat densities, or operation temperature requirements of the plurality of chips.

4. The method of claim 1, wherein the selected chip includes a thermal sensor.

5. The method of claim 1, wherein the measuring the plurality of predetermined temperature parameters associated with the selected chip includes detecting the case temperature above the selected chip.

6. A method performed by an apparatus for testing a multichip module (MCM), the method comprising:
   selecting a chip from a plurality of chips in the MCM;
   measuring a plurality of predetermined temperature parameters associated with the selected chip, the measuring including detecting a junction temperature for the selected chip and a case temperature of the selected chip;
   calculating a thermal resistance value for the MCM using the predetermined temperature parameters, including calculating a difference of the junction temperature and the case temperature, weighted by a total power for the MCM; and
   comparing the MCM to another MCM using the calculated thermal resistance value for the MCM.

7. The method of claim 1, wherein the measuring the plurality of predetermined temperature parameters associated with the selected chip includes detecting the board temperature below the selected chip.

8. A method performed by an apparatus for testing a multichip module (MCM), the method comprising:
   selecting a chip from a plurality of chips in the MCM;
   measuring a plurality of predetermined temperature parameters associated with the selected chip, the measuring including detecting a junction temperature for the selected chip and a board temperature of a board on which the selected chip is mounted;
   calculating a thermal resistance value for the MCM using the predetermined temperature parameters, including calculating a difference of the junction temperature and the board temperature, weighted by a total power for the MCM; and
   comparing the MCM to another MCM using the calculated thermal resistance value for the MCM.

9. The method of claim 1, wherein the measuring the plurality of predetermined temperature parameters associated with the selected chip includes detecting the ambient air temperature.

10. The method of claim 9, wherein calculating the thermal resistance value includes calculating the junction to air thermal resistance.

11. A method performed by an apparatus for testing a multichip module (MCM), the method comprising:
   determining power densities for a plurality of chips in the MCM;
   selecting one of the chips with a higher power density than a remainder of the chips in the plurality of chips in the MCM;
   measuring a plurality of predetermined temperature parameters associated with the selected chip, the measuring including detecting a junction temperature for the selected chip and one or more of:
      an ambient air temperature;
      a case temperature of the selected chip; or
      a board temperature of a board on which the selected chip is mounted;
   calculating a thermal resistance of the MCM using the predetermined temperature parameters, the calculating including calculating one or more of:
      a junction to air thermal resistance as a difference of the junction temperature and the ambient air temperature weighted, by a total power for the MCM;
      a junction to case thermal resistance as a difference of the junction temperature and the case temperature, weighted by the total power for the MCM; or
      a junction to board thermal resistance as a difference of the junction temperature and the board temperature, weighted by the total power for the MCM; and
   comparing the MCM to another MCM using the calculated thermal resistance value for the MCM.

12. The method of claim 11, wherein the predetermined temperature parameters include the case temperature above the selected chip, or the board temperature below the selected chip.

13. The method of claim 11, wherein the thermal resistance is the junction to board thermal resistance.

14. A method performed by an apparatus for testing a multichip module (MCM), the method comprising:
   determining a total power for the MCM;
   selecting a chip from a plurality of chips in the MCM;
   measuring a plurality of predetermined temperature parameters associated with the selected chip, the measuring including detecting a junction temperature for the selected chip and one or more of:
      an ambient air temperature;
      a case temperature of the selected chip; or
      a board temperature of a board on which the selected chip is mounted;
   calculating a thermal resistance of the MCM using the predetermined temperature parameters and the total power for MCM, the calculating including calculating one or more of:
      a junction to air thermal resistance as a difference of the junction temperature and the ambient air temperature, weighted by a total power for the MCM;
      a junction to case thermal resistance as a difference of the junction temperature and the case temperature, weighted by the total power for the MCM; or
      a junction to board thermal resistance as a difference of the junction temperature and the board temperature, weighted by the total power for the MCM; and
   comparing the MCM to another MCM using the calculated thermal resistance value for the MCM.

15. A method performed by an apparatus for testing a multichip module (MCM), the method comprising:
   determining heat densities for a plurality of chips in the MCM;
   selecting a chip from the plurality of chips in the MCM, the selecting the chip comprising selecting the chip with a higher heat density than a remainder of the chips in the plurality of chips in the MCM;
   measuring a plurality of predetermined temperature parameters associated with the selected chip, the measuring including detecting a junction temperature for the selected chip and one or more of:
      an ambient air temperature;
      a case temperature of the selected chip; or
      a board temperature of a board on which the selected chip is mounted;

calculating a thermal resistance of the MCM using the predetermined temperature parameters, the calculating including calculating one or more of:
- a junction to air thermal resistance as a difference of the junction temperature and the ambient air temperature, weighted by a total power for the MCM;
- a junction to case thermal resistance as a difference of the junction temperature and the case temperature, weighted by the total power for the MCM; or
- a junction to board thermal resistance as a difference of the junction temperature and the board temperature, weighted by the total power for the MCM; and comparing the MCM to a second MCM using the calculated thermal resistance value for the MCM.

16. The method of claim 11, further comprising:
obtaining a thermal resistance threshold value, or a second thermal resistance of the second MCM calculated using second predetermined temperature parameters measured for the second MCM; and
the comparing comprising comparing the thermal resistance of the MCM to the thermal resistance threshold value, or to the second thermal resistance of the second MCM.

17. An apparatus comprising:
a multichip module (MCM) device under test (DUT) test board;
at least one processor coupled to the MCM DUT test board via an interface; and
a non-transitory computer readable storage medium storing programming for execution by the at least one processor, the programming including instructions to:
select a chip from a plurality of chips in the MCM;
measure a plurality of predetermined temperature parameters associated with the selected chip using temperature sensors embedded in or thermally coupled to the selected chip, the instructions to measure including instructions to detect a junction temperature for the selected chip and one or more of:
an ambient air temperature;
a case temperature of the selected chip; or
a board temperature of a board on which the selected chip is mounted;
calculate a thermal resistance value for the MCM using the predetermined temperature parameters, the instructions to calculate including instructions to calculate one or more of:
a junction to air thermal resistance as a difference of the junction temperature and the ambient air temperature, weighted by a total power for the MCM;
a junction to case thermal resistance as a difference of the junction temperature and the case temperature, weighted by the total power for the MCM; or
a junction to board thermal resistance as a difference of the junction temperature and the board temperature, weighted by the total power for the MCM; and
compare the MCM to another MCM using the calculated thermal resistance value for the MCM.

18. An apparatus comprising:
a multichip module (MCM) device under test (DUT) test board;
at least one processor coupled to the MCM DUT test board via an interface; and
a non-transitory computer readable storage medium storing programming for execution by the at least one processor, the programming including instructions to:
select a chip from a plurality of chips in the MCM;
measure a plurality of predetermined temperature parameters associated with the selected chip using temperature sensors embedded in or thermally coupled to the selected chip, the instructions to measure including instructions to detect a junction temperature for the selected chip and one or more of:
an ambient air temperature;
a case temperature of the selected chip; or
a board temperature of a board on which the selected chip is mounted;
calculate a thermal resistance value for the MCM using the predetermined temperature parameters, the instructions to calculate including instructions to calculate one or more of:
a junction to air thermal resistance as a difference of the junction temperature and the ambient air temperature, weighted by a total power for the MCM;
a junction to case thermal resistance as a difference of the junction temperature and the case temperature, weighted by the total power for the MCM; or
a junction to board thermal resistance as a difference of the junction temperature and the board temperature, weighted by the total power for the MCM;
obtain a thermal resistance threshold value or other thermal resistance values for other MCMs; and
evaluate the MCM by comparing the thermal resistance value of the MCM with the thermal resistance threshold value or the other thermal resistance values for the other MCMs.

19. An apparatus comprising:
a multichip module (MCM) device under test (DUT) test board;
at least one processor coupled to the MCM DUT test board via an interface; and
a non-transitory computer readable storage medium storing programming for execution by the at least one processor, the programming including instructions to:
determine heat densities for a plurality of chips in the MCM;
select a chip in the MCM with a higher heat density than a remainder of chips in the MCM;
measure a plurality of predetermined temperature parameters associated with the selected chip using temperature sensors embedded in or thermally coupled to the selected chip, the instructions to measure including instructions to detect a junction temperature for the selected chip and one or more of:
an ambient air temperature;
a case temperature of the selected chip; or
a board temperature of a board on which the selected chip is mounted;
calculate a thermal resistance value for the MCM using the predetermined temperature parameters, the instructions to calculate including instructions to calculate one or more of:
a junction to air thermal resistance as a difference of the junction temperature and the ambient air temperature, weighted by a total power for the MCM;
a junction to case thermal resistance as a difference of the junction temperature and the case temperature, weighted by the total power for the MCM; or
a junction to board thermal resistance as a difference of the junction temperature and the board temperature, weighted by the total power for the MCM; and compare the MCM to another MCM using the calculated thermal resistance value for the MCM.

20. An apparatus comprising:

a multichip module (MCM) device under test (DUT) test board;

the MCM mounted on the MCM DUT test board;

at least one processor coupled to the MCM DUT test board via an interface, and coupled to the MCM via the MCM DUT test board and the interface;

a non-transitory computer readable storage medium storing programming for execution by the at least one processor, the programming including instructions to:

select a chip from a plurality of chips in the MCM;

measure a plurality of predetermined temperature parameters associated with the selected chip using temperature sensors embedded in or thermally coupled to the selected chip, the instructions to measure including instructions to detect a junction temperature for the selected chip and one or more of:

an ambient air temperature;

a case temperature of the selected chip; or a board temperature of a board on which the selected chip is mounted;

calculate a thermal resistance value for the MCM using the predetermined temperature parameters, the instructions to calculate including instructions to calculate one or more of:

a junction to air thermal resistance as a difference of the junction temperature and the ambient air temperature, weighted by a total power for the MCM;

a junction to case thermal resistance as a difference of the junction temperature and the case temperature, weighted by the total power for the MCM; or a junction to board thermal resistance as a difference of the junction temperature and the board temperature, weighted by the total power for the MCM; and compare the MCM to another MCM using the calculated thermal resistance value for the MCM.

* * * * *